United States Patent [19]

Farrago

[11] Patent Number: 5,073,986

[45] Date of Patent: Dec. 24, 1991

[54] PAD STRUCTURE FOR RELIEVING KNEE STRESS

[76] Inventor: Douglas M. Farrago, 8807 Heathton Dr., Houston, Tex. 77099

[21] Appl. No.: 562,385

[22] Filed: Aug. 2, 1990

[51] Int. Cl.⁵ .............................................. A41D 13/06
[52] U.S. Cl. ............................................ 2/22; 5/443
[58] Field of Search ................... 2/22, 24, 23; 5/443; 128/80 R, 89 R; 297/423, 438

[56] References Cited

U.S. PATENT DOCUMENTS

| | | | |
|---|---|---|---|
| 3,284,817 | 11/1966 | Landwirth | 128/80 R |
| 3,585,639 | 6/1971 | Enicks | 2/22 |
| 3,693,619 | 9/1972 | Williams | 2/24 |
| 3,901,228 | 8/1975 | Brown | 128/80 R |
| 4,084,584 | 4/1978 | Detty | 2/24 |
| 4,371,985 | 2/1983 | Pokhis | 2/22 |
| 4,377,309 | 3/1983 | Mergshoel | 2/24 |
| 4,392,489 | 7/1983 | Wagner, Sr. | 5/443 |
| 4,441,211 | 4/1984 | Donzis | 2/69 |
| 4,723,322 | 2/1988 | Shelby | 2/24 |
| 4,772,071 | 9/1988 | Richards | 2/24 |
| 4,788,972 | 12/1988 | DeBusk | 128/89 R |
| 4,844,094 | 7/1989 | Grim | 128/80 H |

FOREIGN PATENT DOCUMENTS 7807535  1/1980  Netherlands ..................... 128/80 R Primary Examiner—Werner H. Schroeder
Assistant Examiner—Amy Brooke Vanatta
Attorney, Agent, or Firm—Ben D. Tobor

[57] ABSTRACT

A pad structure for relieving stress to a person's knee and leg has a flexible enclosure substantially filled with a flexible, resilient material, and the flexible enclosure is releasably secured to the person's leg behind the person's knee and in contact with the back of the person's upper and lower leg.

18 Claims, 1 Drawing Sheet

PAD STRUCTURE FOR RELIEVING KNEE STRESS

FIELD OF THE INVENTION

The invention relates to a pad structure for relieving stress to a person's knee and leg, the stress being caused by the person assuming a squatting or kneeling position.

DESCRIPTION OF THE PRIOR ART

In a variety of activities, such as work activity, sports activity, or every day activity, a person's knee and leg muscles may be subjected to stress, sometimes severe stress, caused by a person squatting or kneeling. Examples of such activities include playing the position of catcher on a baseball team, weight lifters performing power squats, installing flooring or roofing, and gardening. In the case of individuals playing the position of catcher on a baseball team, over an extended baseball career, a person can stretch the patella tendon, wear down both menisci in the knee, and irritate many of the bursa sacs needed to lubricate the knee, which irritation can lead to bursitis. Such effects are many times generally referred to as "catcher's knee", but are also applicable to individuals engaged in many occupations which require a person to assume a kneeling or squatting position for extended periods of time.

The main danger at the knee occurs when the center of rotation for knee flexion is altered because of the pressing together of the tissues of the calf and thigh. When the tissues touch, the center of rotation moves back from right at the knee to the area where the tissue of the calf and thigh contact. With the gravity line being located behind the center of rotation, a first class lever with a wrenching, or separating effect at the knee is produced. Although no one has proposed a solution to the problem generally referred to as "catcher's knee" and specifically directed toward individuals playing the position of catcher in baseball, many devices have been proposed to relieve knee stress, particularly directed to individuals involved in an activity that requires kneeling. In particular, various types of knee pads have been proposed; however, such knee pads do not address the problem resulting from the movement of the center of rotation toward where the tissue of the calf and thigh contact. Other devices proposed to alleviate problems associated with kneeling require many different parts which must be adjusted with respect to one another, are bulky and cumbersome, and are believed to be relatively expensive to manufacture. Such devices are particularly not well adapted for use by an individual who must routinely change from a kneeling position to a squatting position, such as a baseball catcher or someone working in his or her garden. Other prior art devices include an inflatable bladder attached to a person's leg; however, such devices are believed to have the disadvantages of lacking durability, require inflation and deflation, and would require repeated repairs as is typical for any type of inflatable article which is subject to much force, such as inflatable pool toys.

Accordingly, prior to the development of the present invention, there has been no pad structure for relieving stress to a person's knee and leg, the stress being caused by a person squatting or kneeling, which: is simple to manufacture and use: is durable: is inexpensive to manufacture: not cumbersome: is comfortable to use: and provides separation between the upper and lower leg of a person when the person assumes a kneeling or squatting position. Therefore, the art has sought a pad structure which: is simple to manufacture and use; is durable; is inexpensive to manufacture: is not cumbersome; is comfortable to use, whether in a standing, kneeling, or squatting position; and prevents the back of the upper and lower legs, or tissue of the calf and thigh, from contacting when the person assumes a squatting or kneeling position.

SUMMARY OF THE INVENTION

In accordance with the invention, the foregoing advantages have been achieved through the present pad structure for relieving stress to a person's knee and leg, the stress being caused by the person squatting or kneeling. The present invention includes: a generally polyhedron shaped flexible enclosure having two side face surfaces and a periphery surface formed by at least three periphery surfaces, a first periphery surface adapted to be disposed adjacent the back of the upper leg of the person, and a second periphery surface adapted to be disposed adjacent the back of the lower leg of the person; the flexible enclosure being substantially filled with a flexible, resilient material; and means for releasably securing the flexible enclosure to the person's leg, whereby the flexible enclosure is disposed behind the person's knee and in contact with the back of the person's upper and lower leg. A further feature of the present invention is that the flexible, resilient material may be an open cell foam. Another feature of the present invention is that the flexible enclosure may be formed of a substantially air impermeable nylon fabric.

A further feature of the present invention is that the flexible, resilient material may be a closed cell foam, rubber material, or synthetic gel material. An additional feature of the present invention is that the periphery surface may be formed by four periphery surfaces, a third periphery surface adapted to be disposed adjacent and spaced from the back of the knee of the person, and a fourth periphery surface disposed opposite the third periphery surface; the first periphery surface having a length which is less than the length of the second periphery surface, and the fourth periphery surface having a length longer than the third periphery surface.

Another feature of the present invention is that the configuration of each side face surface of the generally polyhedron shaped flexible enclosure is a quadrilateral, and the periphery surface is formed by four periphery surfaces, including a third periphery surface adapted to be disposed adjacent and spaced from the back of the knee of the person and the fourth periphery surface may be disposed opposite the third periphery surface. Another feature of the present invention is that the configuration of each side face surface of the generally polyhedron shaped flexible enclosure may he a trapezoid and the third and fourth periphery surfaces are parallel to each other.

The pad structure of the present invention, when compared with previously proposed prior art devices to relieve stress to a person's knee has the advantages of: being simple to manufacture and use: is durable; is inexpensive to manufacture; is not cumbersome and burdensome to the person wearing the pad structure; is comfortable; and keeping a person's upper and lower leg from contacting one another when assuming a squatting or kneeling position.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

Figure 1:
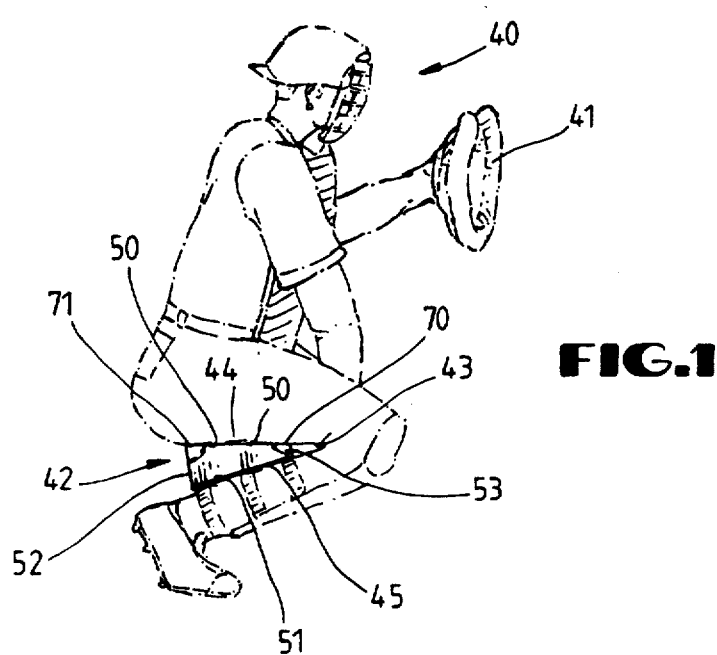
FIG. 1 is a schematic side view of a person playing the position of catcher and assuming the catcher's squatting position, while using the pad structure of the present invention.

In FIG. 1, a person 40 is schematically shown in a typical baseball catcher's squatting position, wherein a person 40 is extending outwardly a catcher's glove 41. The pad structure 42 of the present invention, as will be hereinafter described in greater detail, is disposed adjacent knee 43 and between the upper leg 44 and lower leg 45 of person 40. For drawing clarity, pad structure 42 is illustrated as being slightly spaced from the back of upper and lower legs 44, 45, but a portion of pad structure would contact the back of the thigh, or upper leg, 44, and the back of the calf, or lower leg, 45 when in use. Preferably, person 40 would wear a pad structure 42 on each of his or her legs. As will be hereinafter described in greater detail, pad structure 42 provides a force upon upper and lower legs 44, 45, whereby the back of thigh 44 does not contact the back of calf 45, so that the center of rotation for flexion of knee 43 remains at knee 43. Without pad structure 42, when person 40 assumes the squatting position illustrated in FIG. 1, or a kneeling position (not illustrated) the back of thigh 44 would contact the back of calf 45, whereby the center of rotation for knee 43 flexion would move from knee 43 to a point where the back of upper leg 44 contacts the back of lower leg 45.

Figure 2:
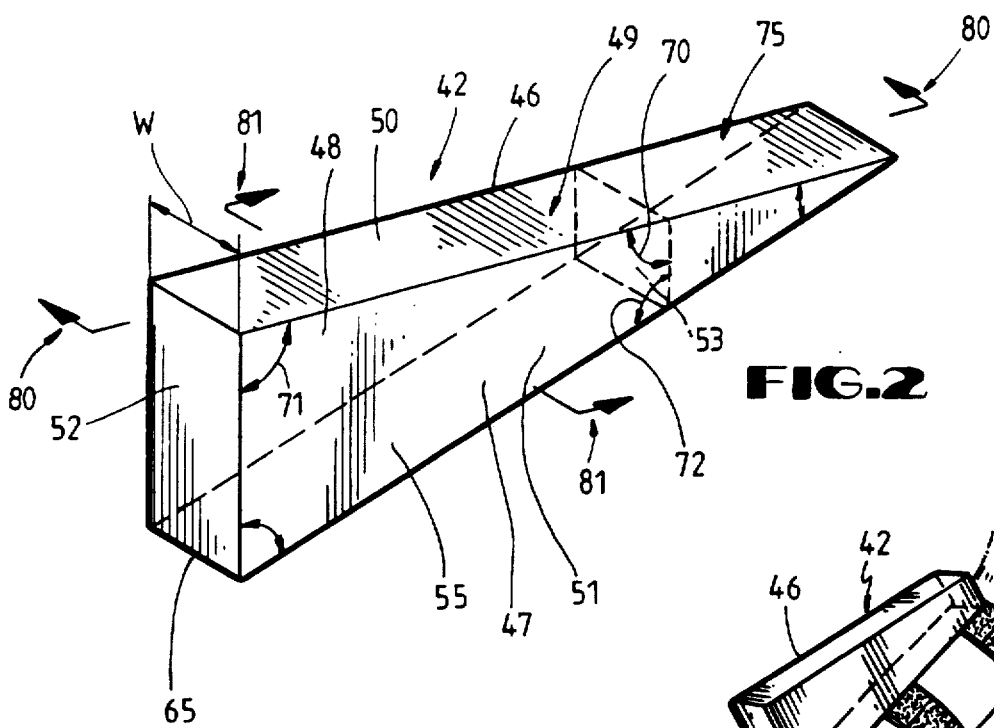
FIG. 2 is a side perspective view of a pad structure in accordance with the present invention.

With reference to FIG. 2, pad structure 42 is seen to generally comprise a generally polyhedron shaped flexible enclosure 46 having two side face surfaces 47, 48 and a periphery surface 49 formed by at least three periphery surfaces 50, 51, 52. As seen in FIGS. 1 and 2, first periphery surface 50 is adapted to be disposed adjacent the back of the upper leg, or thigh 44 of person 40, and the second periphery surface 51 is adapted to be disposed adjacent the back of the lower leg, or calf, 45 of person 40. Flexible enclosure 46 has a general polyhedron shape formed by the substantially planar surfaces 47-52.

Still with reference to FIGS. 1 and 2, flexible enclosure 46 is substantially filled, and preferably completely filled, with a flexible, resilient material 55. When disposed in the position illustrated in FIG. 1, material 55 exerts a force which separates upper and lower legs 44, 45, and thus relieves stress upon knee 43, and is believed to relieve stress caused to the leg muscles of upper and lower legs 44, 45, by maintaining the center of rotation for knee flexion at knee 43. As will be hereinafter described in connection with FIG. 3, pad structure 42 includes means for releasably securing 60 the flexible enclosure 46 to the person's leg 44/45, whereby the flexible enclosure 46 is disposed behind the person's knee 43 and in contact with the back of the person's thigh, or upper leg, 44 and calf, or lower leg, 45.

A variety of flexible, resilient materials 55 may be utilized within flexible enclosure 46. The flexible, resilient material 55 may be an open cell foam, a closed cell foam, natural or synthetic rubber, or a synthetic gel material, all of which are commercially available. Any such materials may be utilized provided they have the requisite strength, resiliency, and durability characteristics to withstand repeated cycles of compression, caused by the person squatting or kneeling, and expansion of the pad structure 42, caused by the person standing up and relieving the force on the pad structure 42. The flexible enclosure 46, as well as the flexible, resilient material 55 therein, both must be durable enough to withstand rough use, and abuse, which would typically be encountered when pad structure 42 is worn by an athlete or a worker engaged in an occupation which requires kneeling or squatting. Furthermore, flexible, resilient material 55 must be capable of providing a force upon the backs of the upper and lower legs 44, 45 to maintain upper and lower legs 44, 45 in a spaced relationship, as well as resist further compression of flexible enclosure 46 and flexible, resilient material 55 by exerting a force to resist the movement of upper leg 44 toward lower leg 45 caused by the person's body weight acting downwardly. Additionally, when pad structure 42 is utilized by such individuals, as well as gardeners, the flexible enclosure 46 should be made of a material which is relatively easy to clean and maintain. Accordingly, flexible enclosure 46 may be manufactured of any suitable material, such as a natural fabric or synthetic fabric material; however, a conventional heavy duty nylon fabric is preferred.

If open cell foam material is utilized for the flexible, resilient material 55, it is preferred to utilize a substantially air impermeable nylon fabric for flexible enclosure 46. Since the cells of an open cell foam material hold a volume of air therein which may be expelled upon a compressive force being exerted upon such open cell foam material, it is preferred that substantially all of the air contained within the open cell foam material 55 remain within the flexible enclosure 46, in order to permit the open cell foam material 55 disposed within flexible enclosure 46 to maintain the necessary force between the upper and lower legs 44, 45 of a person. Alternatively, a portion of the flexible enclosure 46 may be provided with at least one air permeable region 65, which may be a seam at which the nylon fabric material of flexible enclosure 46 is sewn or otherwise secured together. Air permeable region 65 may be provided with a plurality of openings, so that upon application of a force upon pad structure 42 from upper and lower legs 44, 45, some of the air contained within flexible enclosure 46 and the open cell foam material of flexible, resilient material 55, may escape through the air permeable portion 65 of flexible enclosure 46, to permit pad structure 42 to compress slightly. Upon removal of the compressive force exerted upon pad structure 62 by legs 44, 45, the open cell foam material expands and draws air back into pad structure 42, through the air permeable portion 65, in order to assume its original configuration. Such a construction may be ideally suited for an athlete, such as a baseball catcher, or weight lifter doing power squats, in that the athlete initially assumes a squatting position for a brief period of time, and then assumes a standing position, or other position, where no force is exerted upon pad structure 42.

A substantially air impermeable nylon fabric may also be well suited for forming flexible enclosure 46 when a synthetic gel material is utilized as the flexible, resilient material 45. If a natural or synthetic rubber material is utilized as flexible, resilient material 55, any type of fabric material, of natural or synthetic fibers, such as nylon fabric, may be utilized. If a closed cell foam material is used as flexible, resilient material 55, such material may be provided with an outer skin surface, which is obtained in a conventional manner by dipping the closed cell foam material into a conventional protective coating. Alteratively, closed cell foam material may be also disposed within a fabric flexible enclosure 46, such as that previously described.

Still with reference to FIGS. 1 and 2, flexible enclosure 46 may have its periphery surface 49 formed by four periphery surfaces 50-53, a third periphery surface 53 being disposed adjacent and spaced from the back of the knee 43 of person 40. The fourth periphery surface 52 is disposed opposite the third periphery surface 53. As seen in FIGS. 1 and 2, preferably the first periphery surface 50 has a length which is less than the length of the second periphery surface 51, and the fourth periphery surface 52 has a length longer than the third periphery surface 53. Thus, the configuration of each side face surface 47, 48 of flexible enclosure 46 is a quadrilateral configuration. The configuration of each side face surface 47, 48 of flexible enclosure 46 may be a trapezoid shape, whereby the third and fourth periphery surfaces 53, 52 are parallel to each other as seen in FIG. 1. Furthermore, angles 70, 71 may be right angles, whereby third and fourth periphery surfaces 53, 52, are disposed substantially perpendicular to first periphery surface 50. Preferably, angle 72 is a right angle as seen in FIG. 2, in order to increase the amount of volume of flexible enclosure 46 containing flexible, resilient material 55 acting upon the back of upper leg 44. Although pad structure 42 could be formed having a configuration of each side face surface 47, 48 in the shape of a triangle, as illustrated in FIG. 2, it has been determined that pad structure 42 is more comfortable for the wearer of pad structure 42, if the tip 75 of flexible enclosure 46 is removed, or truncated, whereby the third periphery surface 53 is formed by the removal of portion 75 of flexible enclosure 46 to leave flexible enclosure 46 in the configuration illustrated in FIGS. 1 and 3.

It has been determined that in addition to increased comfort resulting from truncating flexible enclosure 46 by removing portion 75, pad structure 42 is more effective in alleviating the dislocating force component which affects the knee joint 43 the further pad structure 42 is placed from knee 43. In this regard, certain sizes of periphery surfaces 50-53 have been found to provide optimum results for different size individuals to obtain optimum relief from the force present on his or her knees. First periphery surface 50 should fall within a range of from four to eighteen inches, and the length of the second periphery surface 51 should fall within a range of from five to twenty inches in length, reference being made to pad structure 42 having the configuration illustrated in FIGS. 1 and 3, or in FIG. 2 with portion 75 of enclosure 46 removed. The length of the third periphery surface 53 should fall within a range of from one-half to five inches, and the length of the fourth periphery surface 52 is within a range of from two to eight inches. The width W of periphery surfaces 50-53 should fall within a range of from two to eight inches. Angle 70 and 71 may fall within the range of from 75 to 110 degrees. In its preferred form, pad structure 42 has the following dimensions. First periphery surface 50 has a length of seven inches. Second periphery surface 51 has a length of 7.8 inches. Third periphery surface 53 has a length of approximately 1 inch, and fourth periphery surface 52 has a length of four inches. The width W of periphery surfaces 50-53 is five inches. Angle 71 is 90 degrees.

When pad structure 42 is viewed along its major longitudinal axis 80, the cross-sectional configuration of flexible enclosure 46 is substantially polygonal shaped, and has at least three periphery surfaces 50-52 as previously discussed. When flexible enclosure 46 is viewed along its minor longitudinal axis 81 (FIG. 2), the cross-sectional configuration of flexible enclosure 46 is substantially rectangular shaped, and generally has the configuration illustrated in FIG. 2 for periphery surface 52.

Figure 3:
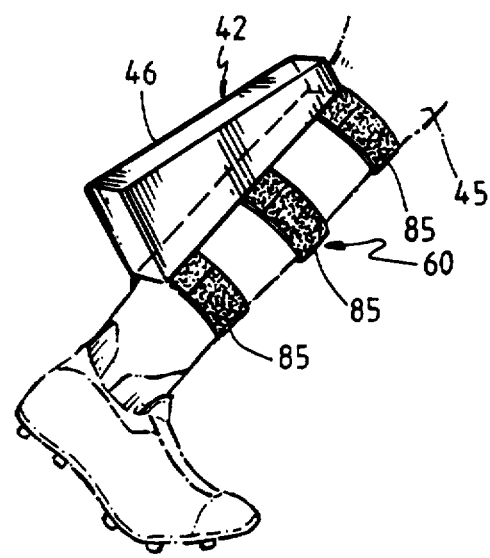
FIG. 3 is a side perspective view of a portion of a person's leg wearing the pad structure of the present invention.

With reference now to FIG. 3, releasable securing means 60 will be described in greater detail. Flexible enclosure 46 has fixedly secured thereto releasable securing means 60 in any conventional manner. For example, releasable securing means 60 may be attached to the fabric material which forms flexible enclosure 46, as by sewing or gluing releasable securing means 60 to flexible enclosure 46. Releasable securing means 60 includes at least one strap member 85 secured to flexible enclosure 46. As illustrated in FIG. 3, three strap members 85 are utilized, which are spaced along periphery surface 51 of pad structure 42. Alternatively, one strap member 85 could be utilized, which strap member has a length which approximates the length of second periphery surface 51 of pad structure 42. Preferably, each strap member 85 is formed in two parts, one part having a hook-like material disposed at its end which engages with an eye-like material disposed at the end of the other part of strap member 85. Such material is sold under the trademark VELCRO ®, whereby the strap members 85 can be readily secured to, and released from, the lower leg 45 of the wearer of pad structure 42. Alternatively, pad structure 42 could be releasably secured to the upper leg, or thigh 44 of the wearer of pad structure 42, or pad structure 42 could be releasably secured to lower leg 45, but with periphery surface 50 contacting the back of lower leg, or calf, 45. In the case of an athlete, such as a baseball catcher wearing pad structure 42, time is of the essence for such an individual putting on and taking off his equipment, and releasably securing means would readily permit pad structure 42 being worn and removed by a baseball catcher. Alternatively, if desired, a baseball catcher wearing pad structure 42 could keep the pad structure 42 on his leg 44, 45, while batting.

It is to be understood that the invention is not limited to the exact details of construction, operation, exact materials or embodiments shown and described, as obvious modifications and equivalents will be apparent to one skilled in the art; for example, the pad structure could be incorporated as an integral part of a baseball catcher's shin guard, or could be clipped or strapped onto a baseball catcher's shin guard. Accordingly, the invention is therefore to be limited only by the scope of the appended claims.

I claim:

1. A pad structure for relieving stress to a person's knee and leg, the stress being caused by the person squatting or kneeling, comprising:
   a generally polyhedron shaped flexible enclosure having two side face surfaces, the configuration of each side face surface being a quadrilateral, and a periphery surface formed by four periphery surfaces, a first periphery surface adapted to be disposed adjacent the back of the upper leg of the person, a second periphery surface adapted to be disposed adjacent the back of the lower leg of the person, a third periphery surface adapted to be disposed adjacent and spaced from the back of the knee of the person and a fourth periphery surface is disposed opposite the third periphery surface;
   all of the periphery surfaces being disposed between the back of the upper leg and the back of the lower leg with no portion of the flexible enclosure being disposed upon the front of the lower leg;
   the flexible enclosure being substantially filled with a flexible, resilient material; and
   means for releasably securing the flexible enclosure to the person's leg, whereby the flexible enclosure is disposed behind the person's knee and in contact with the back of the person's upper and lower leg.

2. The pad structure of claim 1, wherein the flexible, resilient material is an open cell foam.

3. The pad structure of claim 2, wherein the flexible enclosure is formed of a substantially air impermeable nylon fabric.

4. The pad structure of claim 1, wherein the flexible, resilient material is a closed cell foam.

5. The pad structure of claim 2, wherein the flexible, resilient material is a rubber material.

6. The pad structure of claim 1, wherein the flexible, resilient material is a synthetic gel material.

7. The pad structure of claim 1, wherein the flexible, enclosure is formed of a substantially air impermeable nylon fabric, and the flexible resilient material is an open or closed cell foam.

8. The pad structure of claim 1, wherein the first periphery surface has a length which is less than the length of the second periphery surface, and the fourth periphery surface has a length longer than the third periphery surface.

9. The pad structure of claim 1, wherein the length of the first periphery surface is within a range of from four to eighteen inches, and the length of the second periphery surface is within a range of from five to twenty inches.

10. The pad structure of claim 9, wherein the configuration of each side face surface of the generally polyhedron shaped flexible enclosure is a trapezoid and the third and fourth periphery surfaces are parallel to each other.

11. The pad structure of claim 9, wherein the length of the third periphery surface is within a range of from one-half to five inches, and the length of the fourth periphery surface is within a range of from two to eight inches.

12. A pad structure for relieving stress to a person's knee caused by the person squatting or kneeling, comprising:
    a generally polyhedron shaped flexible enclosure having major and minor longitudinal axes, the cross-sectional configuration of the enclosure along its major longitudinal axis being substantially quadrilaterally shaped, having four periphery surfaces, the cross-sectional configuration of the enclosure along its minor longitudinal axis being substantially rectangular shaped, a first periphery surface adapted to be disposed adjacent the back of the upper leg of the person, a second periphery surface adapted to be disposed adjacent the back of the lower leg of the person, a third periphery surface adapted to be disposed adjacent and spaced from the back of the knee of the person and a fourth periphery surface is disposed opposite the third periphery surface;
    all of the periphery surfaces being disposed between the back of the upper leg and the back of the lower leg with no portion of the flexible enclosure being disposed upon the front of the lower leg;
    the flexible enclosure being substantially filled with a flexible, resilient material; and
    means for releasably securing the flexible enclosure to the person's leg, whereby the flexible enclosure is disposed behind the person's knee and in contact with the back of the person's upper and lower leg.

13. The pad structure of claim 12, wherein the flexible, resilient material is an open cell foam.

14. The pad structure of claim 13, wherein the flexible enclosure is formed of a substantially air impermeable nylon fabric.

15. The pad structure of claim 12, wherein the flexible, resilient material is a closed cell foam.

16. The pad structure of claim 12, wherein the flexible, enclosure is formed of a substantially air impermeable nylon fabric, and the flexible, resilient material is an open or closed cell foam.

17. The pad structure of claim 12, wherein the first periphery surface has a length which is less than the length of the second periphery surface, and the fourth periphery surface has a length longer than the third periphery surface.

18. The pad structure of claim 12, wherein the configuration of each side face surface of the generally polyhedron shaped flexible enclosure is a trapezoid and the third and fourth periphery surfaces are parallel to each other.

* * * * *